United States Patent [19]

Schuett

[11] Patent Number: 4,804,790

[45] Date of Patent: Feb. 14, 1989

[54] PROCESS FOR OBTAINING FATTY ALCOHOLS FROM FREE FATTY ACIDS

[75] Inventor: Hartwig Schuett, Duesseldorf-Benrath, Fed. Rep. of Germany

[73] Assignee: Henkel Kommanditgesellschaft auf Aktien, Duesseldorf, Fed. Rep. of Germany

[21] Appl. No.: 133,188

[22] Filed: Dec. 15, 1987

Related U.S. Application Data

[63] Continuation of Ser. No. 859,850, May 1, 1986, abandoned, which is a continuation of Ser. No. 628,702, Jul. 9, 1984, abandoned.

[30] Foreign Application Priority Data

Jul. 14, 1983 [DE] Fed. Rep. of Germany ....... 3325421

[51] Int. Cl.$^4$ .................. C07C 29/136; C07C 31/125
[52] U.S. Cl. ................................................... 568/885
[58] Field of Search ........................................ 568/885

[56] References Cited

U.S. PATENT DOCUMENTS

| | | | |
|---|---|---|---|
| 2,248,465 | 7/1941 | Rittmeister | 568/885 |
| 2,275,152 | 3/1942 | Lazier | 568/885 |
| 2,597,074 | 5/1952 | De Bartholomeis et al. | 568/885 |
| 2,750,429 | 6/1956 | De Nora et al. | 568/885 |
| 3,173,959 | 3/1965 | Rittmeister | 260/638 |
| 3,180,898 | 4/1965 | Eisenlohr et al. | 568/885 |
| 3,193,586 | 7/1965 | Rittmeister | 260/638 |
| 4,259,536 | 3/1981 | Voeste et al. | 568/885 |
| 4,398,039 | 8/1983 | Pesa et al. | 568/885 |

FOREIGN PATENT DOCUMENTS

| | | | |
|---|---|---|---|
| 1146483 | 4/1963 | Fed. Rep. of Germany | 568/885 |
| 975134 | 11/1964 | United Kingdom | 568/885 |

Primary Examiner—J. E. Evans
Attorney, Agent, or Firm—Ernest G. Szoke; Wayne C. Jaeschke; Henry E. Millson, Jr.

[57] ABSTRACT

In the gas-phase hydrogenation of free fatty acids and mixtures thereof with fatty acid esters to fatty alcohols on particulate fixed-bed catalysts based on metal oxides in the presence of an at least 50-fold excess of recycled hydrogen at temperatures of 250° to 350° C. and under pressues of from 200 to 500 bars, acid-sensitive catalysts based on zinc oxide are used and the corrosive effect of the starting materials containing free fatty acids on the catalyst is at least largely prevented by increasing the process temperature within the range indicated and/or by reducing the ratio of starting material to recycled hydrogen.

15 Claims, No Drawings

PROCESS FOR OBTAINING FATTY ALCOHOLS FROM FREE FATTY ACIDS

This application is a contiinuation of application Ser. No. 859,850, filed 5/1/86, now abandoned, which in turn is a continuation of application Ser. No. 628,702, filed 7/9/84, now abandoned.

BACKGROUND OF THE INVENTION

1. Field of the Invention

The present invention relates to a process for the gas-phase hydrogenation of free fatty acids, optionally in admixture with fatty acid esters, to fatty alcohols on particulate fixed-bed metal oxide catalysts.

2. Description of the Prior Art

Fatty alcohols, i.e. predominantly linear monohydric alcohols having chain lengths of 8 and more carbon atoms, and their production are described in detail in the literature, for example in Ullmanns Enzyklopaedie der technischen Chemie, 4th Edition, Vol. 11, pages 427–445. A preferred starting material for their production are the fatty acids or fatty acid mixtures occurring in natural fats and/or oils, which are converted by catalytic hydrogenating reduction into fatty alcohols of corresponding chain length. On an industrial scale, the hydrogenating reduction is normally carried out on fatty acid methyl esters obtained from the natural starting materials by transesterification or by lipolysis and subsequent esterification of the free fatty acid with methanol. The use of the fatty acids to be reduced in the form of their methyl esters protects the catalysts, particularly against aggressive attack by the free carboxyl group, so that on an industrial scale satisfactory volume-time yields can be obtained over sufficiently long periods. Accordingly, native fatty alcohols are now predominantly obtained from fatty acid methyl esters by the gas-phase hydrogenation process in which the distilled methyl esters are passed in the vapor phase over fixed copper-containing mixed-oxide catalysts, together with a large excess of hydrogen, at temperatures of from about 230° to 250° C. and under pressures of from bout 250 to 300 bars. The copper-containing mixed-oxide catalysts produced by co-precipitation using the wet method are used in the form of particulate catalysts or extrudates and are generally reduced in the the direct hydrogenating reduction of the free fatty acids has hitherto been of no real practical significance.

It is known that hydrogenation of free fatty acids to form fatty alcohols can be carried out by the suspension process using copper chromite as catalyst. However, this process is only of any use when the copper chromite catalyst is obtained by decomposition of the copper-ammonium chromate complex initially obtained, followed by washing with acetic acid. Catalyst produced in this way is particularly expensive and, effectively, can only be used for suspension hydrogenation because it is extremely difficult to convert into a fixed-bed catalyst. Acid-washed copper chromite can only be tabletted with considerable difficulty, if at all, and because of this cannot be converted into abrasion-resistant, mechanically stable extrudates or other moldings. Any attempts to induce this solidification by tempering adversely affects the catalytic effect. Attempts to apply acid-washed gel or aluminium oxide, also failed to produce technically useful results. The support peptizes and the catalyst is readily washed off the support. In addition, supported catalysts have other disadvantages compared with solid catalysts.

Fatty acid esters, particularly fatty acid methyl esters, and free fatty acids are frequently mentioned together in the relevant patent literature as starting materials for the hydrogenating reduction to saturated and/or unsaturated fatty alcohols (cf. for example U.S. Pat. Nos. 3,193,586 and 3,173,959 and German application Nos. 2,513,377 and 2,613,226). However, these disclosures should be regarded entirely differently with respect to their practical implementation on an industrial scale, depending on whether the fatty acid methyl esters or the free fatty acids are used as starting material in the hydrogenation stage. The fact is that, hitherto, the considerable advantages of fixed-bed catalysis using solid catalysts have not been successfully developed for processing a starting material consisting of or containing free fatty acids. The corrosive effect of the free acids at elevated temperature and pressure upon the solid catalysts which, basically, have been successfully used in the reduction of methyl esters is so great that, hitherto, no serious consideration has been given to the commercial implementation of the above-mentioned proposals for the reduction of free acids.

In order to enable copper chromite catalyst which has not been washed free from acid, i.e. is more favorably priced, to be used for the hydrogenation of free fatty acids, the following procedure is adopted in practice: Fatty alcohol is introduced in a relatively large quantity into the hydrogenation reactor, after which free fatty acids are fed in under hydrogenation conditions. The small quantitites of fatty acid introduced are initially esterified with the excess of fatty alcohol present in the hydrogenation reactor. This process may be carried out continuously using the less expensive catalysts which have not been washed with acid. However, the process requires disproportionately large reactors and only reaches conversion levels of 96% whereas processes using fixed-bed catalysts achieve conversion levels of 99% and higher.

DESCRIPTION OF THE INVENTION

The process of the invention is based on the surprising discovery that, by carefully controlling certain process conditions, free fatty acids, which have not been esterified with lower monofunctional alcohols, can be reduced to fatty alcohols on solid catalysts by the gas-phase hydrogenation process, using fixed-bed catalysts known to be sensitive to acids. By careful and coordinated control of these process parameters, the corrosive effect of the starting material containing free carboxyl groups is inhibited to such an extent that continuous processes can be carried out for periods of several months using the same catalyst, thus enabling a starting material containing free fatty acid to be used as a practical alternative to the use of esterified acids such as methyl esters.

Accordingly, the object of the present invention is to provide process conditions under which the gasphase hydrogenation of a starting material containing free fatty acids can be carried out on acid-sensitive solid catalysts without any need for the process to be stopped or for the catalyst to be changed after only a short time. Accordingly, the invention seeks in particular to eliminate the need for intermediate conversion of the naturally occurring fatty acd triglycerides into the corresponding fatty acid methyl esters and, instead, to enable the fatty acids to be subjected as such to hydrogenating reduction to fatty alcohols.

Accordingly, the present invention relates to a process for the gas-phase hydrogenation of free fatty acids, optionally in admixture with fatty acid esters, to fatty alcohols on particulate fixed-bed metal oxide catalysts in the presence of a large molar excess of recycled hydrogen, which corresponds to at least approximately 50 times the theoretically necessary quantity, at temperatures in the range of from about 250° to about 350° C. and under pressure of from about 200 to about 500 bars; the process of the invention being carried out with acid-sensitive catalysts based on zinc oxide. In the process of the invention the corrosive effect of the starting material containing free fatty acids upon the catalyst can be mostly if not entirely eliminated by increasing the process temperature within the above-mentioned range and/or by reducing the ratio of starting material to recycled hydrogen.

It has surprisingly been found that by varying and coordinating with each other the two process parametes of process temperature and quantitative ratio of the recycled hydrogen to the starting material, a stable, stationary process state is established in which all the advantages of gas-phase hydrogenation over basically acid-sensitive solid catalysts can be obtained, even where free fatty acids are used, without the process prematurely collapsing through catalyst corrosion or erosion.

In general terms, the following rules apply to the above two parameters: If when carrying out the present process corrosion of the acid-sensitive catalyst by the starting material occurs, which is immediately detectable by the discharge of soap into the reaction product, the reaction temperature has to be raised and/or the quantity of recycled hydrogen has to be increased in relation to the quantity of starting material. By varying these process parameters, the overall reaction conditions can be selected in such a way that the fatty acids to be hydrogenated are passed over the acid catalysts substantially in the vapor phase without any intermediate condensation occurring. Surprisingly, even such unstable fixed-bed catalysts as pure zinc oxide withstand the present process conditions on an industrial scale for several months without any significant decomposition of the solid catalysts occurring. This was in fact totally unexpected becasue zinc oxide is known to react with fatty acids at temperatures as low as 50° C. to form zinc soaps. It is also known that zinc soaps undergo decomposition in the form of decarboxylation at 300° C., even in a hydrogen atmosphere, to form paraffins and olefins. Surprisingly, however, these phenomena do not occur in the process of the invention when pure zinc oxide is used as the catalyst. Hitherto, pure zinc oxide has been regarded as ineffectual for hydrogenation reactions of the present type.

In a first embodiment, therefore, the invention relates to a process wherein saturated and/or unsaturated fatty acids are converted into the corresponding fatty alcohols over pure zinc oxide as solid catalyst. With respect to this catalyst, it is important to ensure that the zinc oxide used shows adequate mechanical stability. Zinc oxide satisfying this requirement is obtainable, for example, by the wet process followed by extrusion and/or tabletting.

The use of pure zinc oxide as a hydrogenation catalyst has considerable economic advantages. It is cheaper than all other known hydrogenation catalysts; it is easy to obtain commercially in particulate form; and, as a catalyst material, does not require any reduction or activation phase. Accordingly, when the zinc oxide catalyst is changed, the continuity of the process does not have to be interrupted by a reduction period. Zinc oxide is largely unaffected by so-called catalyst poisons, such as organically bound chlorine, sulfur, arsenic, or mercury and, accordingly, has considerably longer activity periods than heavy metal catalysts. Zinc oxide does not present any pollution problems of the type created by catalysts containing heavy metals. Finally, zinc oxide can be doped as required with any additives which modify the mechanical and/or catalytic properties of the catalyst material in the required direction, as will be illustrated hereinafter in the discussion of another preferred embodiment of the invention.

Where pure zinc oxide is used as the ctalyst, only the carboxyl group is converted into the corresponding alcohol function in the hydrogenating gas-phase reduction without attacking, for example, any olefinic double bonds present in the starting material by hydrogenation. In this embodiment of the invention, therefore, saturated and/or unsaturated fatty aclohols are obtained as products of the gas-phase hydrogenation reaction, depending upon whether or not the starting material was saturated and/or unsaturated.

A second and particularly preferred embodiment of the process of the invention is concerned with the production of saturated fatty alcohols from fatty acids obtained from fats and/or oils of natural origin. It is known that, depending on their origin, native fats and oils can contain relatively small or even relatively large amounts of olefinically mono- or polyunsaturated fatty acids. In the embodiment of the invention described in the following, fatty acid starting materials such as these of any origin can be converted into saturated faatty alcohols. Solid catalysts based on zinc oxide which, through suitable doping, also bring about the catalytic hydrogenation of olefinic double bonds in the starting material are used in this embodiment of the invention. The doping component preferably used herein is copper. Doping is carried out with either soluble or insoluble copper salts. In the initial phase of the gas-phase hydrogenation process of the invention, the copper component is apparently reduced to metallic copper which then brings about hydrogenation of the olefinic double bonds.

The amount of copper in the fixed-bed catalyst is preferably kept relatively small. More particularly, it should not comprise more than about 15% by weight and preferably no more than about 10% by weight, expressed as copper metal and based on the total weight of the solid catalyst. Copper contents of from about 1 to about 5% by weight are particularly suitable. This limitation of the copper content in the solid catalyst results from the following, hitherto unreported observations:

The temperature range in which free fatty acids can be passed over solid catalysts based on zinc oxide, without any corrosive effect upon the catalyst material, generally requires comparatively high temperatures, for example above 290° C. and, more particularly, above 300° C. However, copper as the catalyst component for the hydrogenation of olefinic double bonds is active at temperatures lower by about 100° C. Accordingly, where copper-containing catalysts are used, the need to operate at such comparatively high reaction temperatures results in the formation of undesirably large quantities of paraffinsas reaction products in the final reduction step. However, by limiting the copper content of the catalyst material, an equilibrium state is established wherein a balanced reduction of the carboxyl group to the hydroxyl group and of the olefinic double bond to the saturated carbon bond is possible. However, the use of copper as the doping component in the present catalysts may necessitate a special procedure in the initial stages of a catalyst batch, as will be discussed in detail hereinafter.

In addition, it may be of advantage in accordance with the invention to incorporate stability-promoting additives in the present zinc oxide based catalysts. Zinc oxide/chromium oxide catalysts preferably containing chromium-(III) oxide are particularly suitable for that purpose. Catalyst materials which contain zinc oxide and chromium-(III) oxide in spinel form and which have been doped with the small quantities of copper show particularly good stability. In the preferred embodiment, the chromium oxide content should not exceed the quantity required for spinel formation. In general, it is preferred to use catalyst materials containing zinc oxide in an at least slight excess. The catalysts are produced in a known manner. In the wet process, mixed oxides are formed, for example, from zinc salts and chromium-(VI) salts and are then converted by reduction into the zinc oxide/chromium-(III) oxide spinels.

For long term operation, the process of the invention is normally carried out at temperatures of at least about 270° C. and preferably at temperatures of at least about 290° C. The upper temperature limit is preferably at about 330° C., and more preferably at about 320° C. Temperatures in the range of from about 290 to about 320° C. are particularly suitable, with temperature in the range of from about 300° to 315° C. being especially suitable.

The use of copper-containing catalysts leads to a two-stage activity phase. Immediately after their reduction, catalysts such as these function optimally at the comparatively low temperatures of about 270 to about 285° C., allowing the highest hourly throughputs, i.e. the best volume-time yields. In this activity phase, which at best lasts only about 100 to 200 hours, the copper zinc oxide appears to act to a large extent as a substance hydrogenating carbonyl groups in the classical sense until it is subsequently inactivated by heat and/or poisoning to such an extent that the hydrogenation results are no longer satisfactory. In that event, the hydrogenation temperature has to be increased in a short time, usually within a few hours, by up to 50° C. or more until satisfactory carbonyl-group-hydrogenating activity has been re-established. At that temperature level, the now passivated copperzinc would appear to be active solely in saturating double bonds while the zinc oxide present in excess effects reduction of the carboxyl group to the hydroxyl group. Even in this instance, however, the high temperature level adjusted after the comparatively brief initial phase provides—as required in accordance with the invention—reliable establishment of the combination of process conditions under which the basically acid-sensitive catalyst material has the required long useful life.

By monitoring the quality of the end product, it is readily possible, in coordination with the ratio of recycled hydrogen to starting material, to select the correct temperature: Excessively low process temperatures promote corrosion of the fixed-bed catalyst and hence the discharge of metal soaps into the reaction product. Both zinc soaps and copper soaps can accumulate. Excessively high process temperatures result in overreduction and, hence, in the undesirably extensive formation of paraffins. Any irregularities in the initial phase of a catalyst batch can be readily corrected by monitoring the saponification numbers (SN) and/or the iodine numbers (IN) of the end products.

The reaction temperature which is adjusted to the individual reaction is also co-determined by the length of the carbon chains of the starting material to be reduced. The shorter the chain length of the fatty acids used, the lower the reaction temperatures generally have to be within the ranges given above.

The recycled hydrogen is used in a large excess, which normally amounts to between about 50 and about 500 times the theoretical molar quantity of hydrogen. The recycled hydrogen is preferably used in an excess of about 75 to about 250 times the stoichiometrically necessary quantity. Through this second parameter governing the process of the invention, a temperature range within which the free fatty acids do not have any significant corrosive effect upon the basically acid sensitive catalyst material can be readily determined. As a general rule, it can be said that the occurrence of metal soaps in the reaction product can be suppressed by a relatively high ratio of hydrogen to starting material, which thus has the same beneficial effect as the increase in temperature.

It can be of advantage in the process of the invention to use ratios by volume of liquid starting product to recycled hydrogen under pressure in the range from about 1:50 to about 1:150.

Although evaporation aids, such as lower alcohols, low-boiling paraffins or steam can be added in accordance with the invention to the aatty acid starting material, hydrogenation is carried out in the absence of such additives in the preferred embodiment of the process. On the contrary, provision is made in this preferred embodiment for the gaseous secondary products formed also to be removed from the reaction system and, more particularly, from the recycled gas. These gaseous secondary products are, in particular, small quanitites of lower hydrocarbons, particularly methane, and also the quantities of nitrogen inevitably introduced with the further hydrogen added. In the preferred embodiment, the hydrogen content of the recycled gas should amount to at least 90% by volume and, more particulrly, to at least about 95% by volume.

The process is generally carried out under pressures of 200 bars and higher and, more particularly, under pressures of from about 200 to about 500 bars. Pressures in the range from about 230 to about 350 bars are particularly suitable. In principle, the use of higher pressures results in a reduction in the saponification number of the reaction product and hence in an increase in the yield of desired fatty alcohols.

During the running-in of a fresh catalyst batch, an overreaction initially takes place for a limited period, which generally amounts to no more than a few hours or at most days, due to the high catalytic actvity of the copper component formed in the initial phase. After this brief initial phase, the activity of the catalyst stabilizes, enabling the temperature to be increased as required, for example to between about 290 and about 320° C., so that the corrosive effect of the fatty acid starting material upon the catalyst material can be reliably prevented. The process conditions can readily be controlled in such a way that, overall, satisfactory product parameters can be obtained. Thus, it is possible for example to adjust saponification numbers (SN) in the reaction product to below 2 and, more particularly, below 1; for iodine numbers (IN) of far below 1; while the paraffin content is no greater than at most 1 to 1.5% by weight; and the acid number (AN) of the end product is in the range of from 0.02 to 0.04. The water of reaction is removed from the circuit together with this crude reaction product. After the removal of water and drying, the fatty alcohol formed can be used, optionally after addition or filtration, without any need for additional distillation.

It is also best to coordinate the quantity of fatty acid starting material and the catalyst volume with one another. If the quantity of catalyst is too large, overhydrogenation readily takes place and cannot be corrected by reducing the temperature because this would promote the corrosive effect of the acidic starting material upon the catalyst. If the quantity of catalyst is too small, the acidic starting material may indeed be safely transported through the catalyst without any corrosive effect, but reduction to the fatty alcohol is inadequate. Suitable ratios by volume of the liquid starting material per hour to the volume of catalyst amount to between about 1:2 and about 1:10 and, preferably, to between about 1:3 and about 1:6.

The excess hydrogen which is not used in the hydrogenation reaction is continuously recycled through heat exchangers and only the hydrogen consumed is replaced with fresh hydrogen.

Saturated and/or unsaturated fatty acids containing a uniform number of carbon atoms or fatty acid mixtures can be used as the fatty acid starting material. Particularly sutable fatty acid starting materials are crude $C_8$–$C_{24}$ fatty acid mixtures which have been obtained, for example, by lipolysis from animal and/or vegetable fats and/or oils. If the fatty acids are present in admixture with fatty acid esters, such esters are the corresponding fatty acid esters of lower aliphatic monoalcohols, particularly methanol.

Some catalyst formulations for carrying out the process of the invention, which are particularly suitable copper-containing catalysts based on zinc oxide and which are used in Examples 1 to 4, are described below.

Catalyst Formulations 1. 112 kg of copper sulfate pentahydrate and 112 kg of zinc sulfate heptahydrate are dissolved in 900 liters of tapwater in a salt dissolver and the resulting solution filtered until clear. This solution is run cold into a stirred solution heated to 30° C. of 140 kg of calcined soda in 1750 liters of tapwater; basic copper zinc carbonate being precipitated. By the direct introduction of steam, the suspension is then heated over a period of 1 hour to 50° C.; while undergoing a change in color from blue to green. The basic carbonate mixture is then filtered in filter presses and washed with fully deionized water until the washing water flowing off is free from sulfate. The filter cake is dried at a maximum temperature of 100° C. and then powdered as finely as possible.

10 kg of the powder thus obtained are dry-mixed in a kneader with 10 kg of zinc oxide powder, after which a solution of 15 kg of chromic acid anhydride in 15 kg of deionized water is introduced into the kneader with stirring over a period of a few minutes. These operations have to be carried out with effective dust extraction. Finally, the kneaded mixture becomes increasingly more difficult to knead through evolution of heat and carbon dioxide so that the dough-like mass has to be emptied. It is dried at 100° C. in a shelf dryer, ground and compressed with graphite to form tablets or other compacts. It may even be extruded before drying to form extrudates which are subsequently dried.

The catalyst thus obtained has to be activated. To that end, it is introduced into a heatable reaction furnace which is connected by pipes to a gas recirculating pump and to separators. The system can be operated in the absence of pressure and is initially filled with nitrogen. After a temperature of 280° C. has been reached, initially small quantities of hydrogen and, subsequently, increasing quantities are introduced into the nitrogen circuit under temperature control, the hydrogen initially being rapidly consumed and, subsequently, more slowly consumed for reducing the hexavalent chromium compounds to Cr-(III) compounds, accompanied by reduction of the copper-(II) compounds to finely divided copper metal. The carbonates of the zinc change into oxide mixtures and, in addition to nitrogen, water and carbon dioxide accumulate in the gas mixture. The water is removed by condensation and, in addition to controlling temperature, is used for monitoring progress during reduction of the catalyst. The temperature should be regulated by the introduction of hydrogen in such a way that the temperatures occurring during this operation are no higher than 350° C., even locally, because otherwise the activity of the catalyst will suffer.

The activated zinc-copper-chromium catalyst thus produced has high mechanical strength. its lateral compressive strength (as measured for example on a 6 mm tablet) being >25 kp. It is well capable of withstanding mechanical loads in the following hydrogenation step and does not show any tendency towards abrasion, provided the hydrogenation conditions of the invention are maintained.

2. In a formulation for the production of the hydrogenation catalyst which is even more suitable for many applications, 6.65 kg of the copper-zinc carbonate powder obtained in accordance with formulation 1. above and 13.35 kg of zinc oxide are mixed in powder form and the resulting mixture kneaded with a solution of 15 kg of chromic acid anhydride in 15 kg of water. The procedure used thereafter is the same as in 1. above. This catalyst has even greater strength properties and can be used with advantage in reactions where fatty acids relatively low in sulfur are used. Fatty acids such as these are understood to be fatty acid distillates containing at most 20 ppm of sulfur. If the content of the sulfur compounds acting as catalyst poisons are over that limit, it is best to start out from the catalyst used in formulation 1. so that the life expectancy of the catalyst as it becomes gradually damaged is considerably prolonged. 3. In another alternative formulation for producing the hydrogenation catalyst, 5 kg of commercially available copper chromite powder which has not been washed with acid and 15 kg of zinc oxide are mixed in powder form and kneaded with a solution of 15 kg of chromic acid anhydride and 2 kg of potassium dichromate in 17 kg of water. This mixture is further treated in the same way as in formulation 2. The advantage of this catalyst is that, after the activation phase, it reacts with greater moderation and avoids increased overhydrogenation to paraffins, which usually occurs in the first 5 days of operation. After activation all the catalysts given above have unusually long useful lives, which is considerably longer even than the useful life of known catalysts of the type normally used for the hydrogenation of fatty acid methyl esters to saturated fatty alcohols.

The invention will be illustrated by the following examples which are given for that purpose only and not for purposes of limitation.

EXAMPLES

Example 1

700 g of catalyst produced in accordance with formulation 3. above were introduced into a continuous recycle-gas pilot plant having a reactor volume of 1 liter and activated as described above. Thereafter, 100 ml/h of pure lauric acid, which had been preheated to 240° C., was passed over the catalyst in the presence of hydrogen recirculated at a rate of 16 l/h under a pressure of 250 bars (corresponding to 4 $m^3$/h in the absence of pressure; equal to a 178.5-fold molar excess) at 270° C. Most of the lauric acid evaporated on the catalyst. The hydrogen leaving the reactor was cooled to about 60° C., the hydrogenation product separating and being relieved of pressure. 1 kg of lauric acid produced 920 g of pure lauryl alcohol which accumulated in colorless form with a saponification number of 0.5, an acid number of 0.06, a paraffin content of 0.96% and a low water content. After drying, its hydroxyl number was 299. The aldehyde content of 215 ppm of CO was very low. After about 140 hours' operation under the described conditions, the saponification number rose to 5.2. Because of this, the reactor entry temperature (reaction temperature) was increased to 300° C., as a result of which the saponification number fell below 1.

In the course of the next few days, the reaction temperature was increased to 305° C. The product characteristics set forth above were thus reestablished, remaining unchanged for several weeks until the test was terminated.

Example 2

22.8 kg of a catalyst which had been produced in accordance with formulation 1 and compressed into 6 mm tablets were introduced into a continuous recycle-gas pilot plant having a reactor volume of 17 liters. This catalyst was activated as described above, after which 4.5 l/h of a coconut oil fatty acid fraction ($C_{12}$–$C_{18}$; AN 255; MW 222) were passed over the catalyst, after it had been preheated to 265° C. by heat exchange and by additional heating, in the presence of hydrogen under a pressure of 250 bars recirculated at a rate of 200 l/h (corresponding to 50 $m^3$, i.e. to a 56-fold molar excess) at a temperature of 270° C. The coconut oil fatty acid fraction corresponded to the respective proportions of ingredients in natural coconut oil (2% capric acid, 54% lauric acid, 21% myristic acid, 10% palmitic acid, 3% stearic acid, 9% oleic acid and 1% linoleic acid) and had an iodine number of 12. The reaction mixture of hydrogen, steam and fatty alcohol leaving the reactor was cooled to 50° C. in a heat exchanger and by subsequent cooling, fatty alcohol and water separated and expanded in liquid form to normal pressure. The fatty alcohol freed from the water was water-white and clear and 98% pure and had the following characteristics: AN 0.03; SN 0.6; IN 0.11; OHN 271; solidification point 19° C.; hydrocarbon content 1.6%, and was thus substantially pure. Once again, the reaction temperature had to be rapidly increased after 200 hours' operation to 298° C. at the reactor entrance and to 305° C. at the reactor exit to keep the SN below 1. However, the OHN then rose to 274 and the hydrocarbon content fell to 1.2%. Under these conditions, the product characteristics were kept constant for several weeks.

Example 3

7500 kg of a catalyst which had been produced in accordance with formulation 1. and compressed into 6-mm tablets were introduced into a continous recycle-gas hydrogenation plant having a reactor volume of 5 cubic meters. After activation of the catalyst, 850 l/h of a fatty acid mixture of 70% of lauric acid and 30% of myristic acid having an iodine number of 1.4, which had been preheated to 270° C. by heat exchange and by additional heating, were passed over the catalyst in the presence of hydrogen under a pressure of 250 bars circulated at a rate of 140 $m^3$/h at a temperature of 280° C. The liquid reaction product, expanded from the recirculation system after cooling, was continuously dried and was then water-white and clear; 98.5% thereof consisting of fatty alcohols. It had the following characteristics: AN=0.03; SN=0.95; IN=0.12; OHN=282; solidification point=18° C., hydrocarbon content=1.2%; carbonyl content=198 ppm of CO. This procedure corresponds to a 218-fold molar excess of hydrogen beyond the theoretically necessary quantity. After 6 days' operation, the reaction temperature had to be rapidly increased to 297° C. at the reactor entrance, producing a reactor exit temperature of 305° C. After passing through a dryer, the hydrogenation product had the following characteristics: AN=0.04; SN=1.2; IN=0.42; OHN=285; solidification point 18° C.; hydrocarbon content=1.3%; carbonyl content=226 ppm CO.

Example 4

A fatty acid mixture known as palmolein was introduced into a continuous recycle-gas pilot plant having a reactor volume of 40 l, of which the two hydrogenation reactors arranged one behind the other were filled with 28 kg of a catalyst which had been produced in accordance with formulation 2. The fatty acid mixture (palmolein) consisted of 5% palmitic acid, 75% oleic acid, 17% linoleic acid, 0.5% linolenic acid, 1% stearic acid and 0.5% non-hydrolyzable fractions and had an iodine number of 95.8. After activation of the catalyst, 1250 l/h of hydrogen under a pressure of 250 bars were recirculated at 286° C. and 5 kg/h or palmolein (MW 282), which had been preheated to 280° C. in a heat exchanger and by additional heating, were introduced. This corresponds to a 394-fold molar excess of hydrogen beyond the theoretically necessary quantity. After expansion and removal of the water of reaction, the reaction mixture had a weight of 4.75 kg/hour and a hydroxyl number of 212, an iodine number of 0.44, a saponification number of 1.4, an acid number of 0.04 and a carbonyl content of 96 ppm CO/g. The hydrocarbon content amounted to 1.8%. After 120 hours' operation, the iodine number rose above 2.0 and the reaction temperature was slowly increased to 305° C., as a result of which the iodine number of the hydrogenation product fell back below 1.0 with otherwise the same characteristics. Subsequently, the hourly throughput was increased to 10 kg.

Example 5

1 kg of extruded and thermally compacted zinc oxide of the type industrially used for dehydrogenation processes was introduced into the 1.2-liter reactor of a pilot recycle-gas plant and heated under hydrogen to 300° C. 4 Nm³/h of pure hydrogen was then passed through the reactor under a pressure of 250 bars and at a temperature of 290° C. After stable conditions had been established, 200 ml/h of lauric acid distillate containing 70% lauric acid and 30% myristic acid was pumped under pressure into the hydrogen pipe at a sufficient distance from the reactor entrance. The distance from the point of introduction of the fatty acid to the reactor entrance must be large enough to guarantee complete evaporation of the fatty acid, which in the present case was achieved by a pipe length of 1 m. After the removal of 7% of water of reaction and filtration, the hydrogenation product expanded from the separator of this plant had the following characteristics: AN=0.09; SN=7.1; OHN=232; IN=0.6; carbonyl content=167 ppm CO; hydrocarbons=1.6%, and was thus substantially pure $C_{12}$-$C_{14}$ fatty alcohol.

Example 6

1 kg of particulate zinc oxide was impregnated as uniformly as possible with 20 g of copper acetate in water and dried. It was then introduced into the recycle-gas plant described in Example 5 in which 100 ml/h of acid distillate, consisting of 2% lauric acid, 5% myristic acid, 12% palmitic acid, 75% oleic acid, 4% linoleic acid, 1% linolenic acid, 1% arachic acid, were pumped over the catalyst under pressure at a temperature of 300° C. The acid had been preheated in the same way to 300° C. After removal of the water of reaction and filtration, the hydrogenation product expanded from the separator of this hydrogenation plant had the following characteristics: AN=0.04; SN=1.6; IN=13; OHN=204; carbonyl content=240 ppm CO; hydrocarbon content 1.8%, and was found by gas chromatography to consist of approx. 2% lauryl alcohol, 5% myristyl alcohol, 12% cetyl alcohol, 70% stearyl alcohol, 10% oleyl alcohol and 1% arachyl alcohol.

Example 7

1 kg of extruded and thermally compacted zinc oxide was impregnated by spraying with a 20% aqueous copper acetate solution in such a way that, after drying, the catalyst compact contained approx. 2% copper. 800 g of the catalyst were introduced into a 1-liter reactor of a pilot recycle-gas plant and reduced with hydrogen under nitrogen in the absence of pressure at 250° C. 4 Nm³/h of pure hydrogen were then passed through the plant and over the catalyst at a temperature of 310° C. and under a pressure of 250 bars. After stable conditions had been established, 200 ml/h of coconut oil fatty acid $C_8$-$C_{18}$ i. e. corresponding to the composition of the fatty acids naturally occurring in coconut oil, was passed over the catalyst. The coconut oil fatty acid used had an iodine number of 10 and an acid number of 270, a saponification number of 273 and a solidification point of 23° C. The hydrogenation product accumulating under these conditions had the following characteristics: AN=0.08; SN=4.8; IN=1.4; SP=12° C.; hydrocarbon content=3.2, and was thus substantially pure fatty alcohol with the composition corresponding to that of coconut oil.

Comparison Example 1

A continuous gas recirculation pilot hydrogenation plant comprising 4 individual pressure reactors each 2 liters in volume arranged one behind the other was filled with a catalyst produced in accordance with formulation 1. above which was then activated by reduction under pressure under the same conditions. This plant, which was operated under substantially uniform conditions for 4 weeks at 300° C./250 bars with a recycle gas throughput of 160 l/h, was charged with 4 l/h of 98–100% lauric acid and produced hydrogenation products characterized by an AN of 0.01, an SN of 3.0 and an OHN of 296. With this procedure a 55 x molar excess of recycle gas was maintained. This excess of recycle gas was then reduced to 25-fold by reducing the throughput of recycle gas from 160 l/h to 80 l/h. After 2 hours, the differential pressure of 5 bars in the plant rose beyond 50 bars and the gas recirculation pump had to be switched off because of overloading. After cooling and opening of the reactors, it was found that the catalyst filling in all four reactors had agglomerated into a sticky mass which consisted to a large extent of zinc laurate and which had blocked the reactors.

Comparison Example 2

The same plant as in Comparison Example 1 was filled with a catalyst obtained and activated in the same way as for formulation 3. above. The plant was then charged with 4 l/h of 98% lauric acid at 250° C./250 bars with a recycled gas throughput of 160 l/h. In the first few days of operation, this catalyst requires lower hydrogenation temperatures of from about 270 to 280° C. in order to limit the formation of hydrocarbon caused by excessive activity. In an effort to minimize paraffin formation, the hydrogenation temperature under the described conditions was lowered too far. After several hours, the initially satisfactory (AN 0.04, SN 1.9) and water-white, clear hydrogenation product became increasingly soapy and clouded until it hardened completely on cooling through the separation of solid zinc soap. The hydrogenation temperature was increased to 290° C. and then to 300° C., after which the hydrogenation product became satisfactorily clear again. It was found that the clouded hydrogenation fractions also contained copper soap. This should be strictly avoided because, in the event of subsequent distillation of the lauryl alcohol, relatively large quantities of the unwanted lauryl aldehyde would be formed through dehydrogenation.

What is claimed is:

1. A process for the gas-phase hydrogenation of a free fatty acid to the corresponding fatty alcohol comprising the steps of
   (a) reacting said free fatty acid in the vapor phase in the presence of a particulate fixed-bed, zinc-oxide based, acid-sensitive catalyst containing zinc oxide in excess over other materials present and consisting of either (i) zinc oxide, (ii) zinc oxide and copper, (iii) zinc oxide and chromium III oxide, or (iv) zinc oxide, copper, and chromium III oxide, with hydrogen gas in an amount of from about 75 to about 500 times the theoretical quantity required to reduce said free fatty acid to the corresponding alcohol at a temperature in the range of from about 250° to about 350° C. and at a pressure of from about 200 to about 500 bars; and
   (b) adjusting as needed within the parameters given in (a) either or both of (i) the temperature and (ii) the ratio of free fatty acid to hydrogen, to suppress formation of soap resulting from corrosion of the catalyst and to suppress formation of paraffins resulting from overreduction of fatty acid.

2. A process in accordance with claim 1 wherein the catalyst is a copper-doped zinc oxide catalyst having a copper content of not greater than about 15% by weight thereof.

3. A process in accordance with claim 2 wherein the copper content of the catalyst is below 10% by weight thereof.

4. A process in accordance with claim 2 wherein the copper content of the catalyst is from about 1 to about 5% by weight thereof.

5. A process in accordance with claim 1 wherein the catalyst is a copper-doped zinc oxide/chromium (III) oxide mixed catalyst.

6. A process in accordance with claim 5 wherein the catalyst is in the form of a zinc/chromium spinel.

7. A process in accordance with claim 1 wherein the reaction is carried out until the activity of the catalyst becomes stable, whereupon the reaction temperature is thereafter maintained in the range of from about 290° to about 320° C.

8. A process in accordance with claim 7 wherein the temperature is thereafter maintained in the range of from about 300° to about 315° C.

9. A process in accordance with claim 1 wherein the hydrogen gas is recycled through the process.

10. A process in accordance with claim 1 wherein the hydrogen gas is present in from about 75 to about 250 times the theoretical quantity required to reduce said free fatty acids or ester admixture.

11. A process in accordance with claim 1 wherein the reaction is carried out in the substantial absence of free lower alcohols and inert gases, and wherein secondary reaction products are removed from the reaction system.

12. A process in accordance with claim 9 wherein the hydrogen content of the recycled hydrogen gas is maintained above about 90% by volume.

13. A process in accordance with claim 12 wherein said hydrogen content is maintained above about 95% by volume.

14. A process in accordance with claim 1 wherein the ratio by volume of free fatty acid per hour to the catalyst is from about 1:2 to about 1:6.

15. A process in accordance with claim 1 wherein the fatty acids used therein are crude $C_6$-$C_{24}$ fatty acid mixtures which have been obtained from one or more of animal fats, vegetable fats, and vegetable oils.

* * * * *